(12) United States Patent
Itamochi et al.

(10) Patent No.: US 11,911,550 B2
(45) Date of Patent: Feb. 27, 2024

(54) PRESSURE MEASURING DEVICE AND EXTRACORPOREAL CIRCULATOR

(71) Applicant: TERUMO KABUSHIKI KAISHA, Tokyo (JP)

(72) Inventors: Yosuke Itamochi, Kanagawa (JP); Kozo Hisamatsu, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 1093 days.

(21) Appl. No.: 16/733,003

(22) Filed: Jan. 2, 2020

(65) Prior Publication Data

US 2020/0139040 A1    May 7, 2020

Related U.S. Application Data

(63) Continuation of application No. PCT/JP2018/025493, filed on Jul. 5, 2018.

(30) Foreign Application Priority Data

Jul. 10, 2017  (JP) .................................. 2017-134749

(51) Int. Cl.
 *A61B 8/00* (2006.01)
 *A61M 1/36* (2006.01)
 (Continued)

(52) U.S. Cl.
 CPC ........ *A61M 1/3639* (2013.01); *A61M 1/1698* (2013.01); *A61M 1/262* (2014.02); *A61M 1/3626* (2013.01); *H04N 23/54* (2023.01)

(58) Field of Classification Search
 CPC .. A61M 1/3639; A61M 1/262; A61M 1/1698; A61M 1/3626
 See application file for complete search history.

(56) References Cited

U.S. PATENT DOCUMENTS

| 4,911,015 A | 3/1990 | Miller |
| 7,748,275 B2 | 7/2010 | Kouda et al. |

(Continued)

FOREIGN PATENT DOCUMENTS

| DE | 202004020869 U1 | 3/2006 |
| DE | 102015121455 A1 | 6/2017 |

(Continued)

OTHER PUBLICATIONS

Extended European Search Report, EP18831400.9, dated Feb. 23, 2021.

(Continued)

*Primary Examiner* — Joel F Brutus
(74) *Attorney, Agent, or Firm* — MacMillan, Sobanski & Todd, LLC

(57) ABSTRACT

A pressure measuring device 30 installs on a tube 11 for transferring a medium BL so as to measure a pressure of the medium BL inside the tube 11. The pressure measuring device 30 includes a main body portion 31 mountable to the tube 11, polarizing means 34 disposed in the main body portion 31 so that light oscillating in a specific direction is transmitted therethrough, an image acquisition unit 32 disposed in the main body portion 31 so that image information on a pressure receiver that is deformed in response to the received pressure is acquired through the polarizing means 34, and a control unit 100 that converts the image information acquired by the image acquisition unit 32 into pressure information about the pressure.

13 Claims, 5 Drawing Sheets

(51) Int. Cl.
     *A61M 1/26*          (2006.01)
     *A61M 1/16*          (2006.01)
     *H04N 23/54*        (2023.01)

(56) References Cited

U.S. PATENT DOCUMENTS

| | | | |
|---|---|---|---|
| 2009/0009764 A1 | 1/2009 | Slepicka | |
| 2012/0065596 A1* | 3/2012 | Haueter | G01L 9/0077 |
| | | | 604/246 |
| 2013/0036824 A1 | 2/2013 | Chung et al. | |
| 2014/0030149 A1* | 1/2014 | Takeuchi | A61M 1/3623 |
| | | | 422/48 |
| 2018/0272055 A1 | 9/2018 | Itamochi et al. | |

FOREIGN PATENT DOCUMENTS

| | | |
|---|---|---|
| GB | 2223094 A | 3/1990 |
| JP | S5728347 U | 2/1982 |
| JP | 09229799 A | 9/1997 |
| JP | 3201948 U | 1/2016 |

OTHER PUBLICATIONS

Written Opinion of the International Searching Authority, PCT/JP2018/025493, dated Aug. 7, 2018.
Japanese Office Action, 2019-529093, dated Jun. 1, 2022.
International Search Report, PCT/JP2018/025493, dated Aug. 7, 2018.

* cited by examiner

PRESSURE MEASURING DEVICE AND EXTRACORPOREAL CIRCULATOR

CROSS REFERENCE TO RELATED APPLICATIONS

This application is a continuation of PCT Application No. PCT/JP2018/025493, filed Jul. 5, 2018, based on and claiming priority to Japanese Application No. 2017-134749, filed Jul. 10, 2017, both of which are incorporated herein by reference in their entirety.

BACKGROUND OF THE INVENTION

The present invention relates to a pressure measuring device which is mounted to a tube allowing a medium such as blood to pass therethrough so as to measure a pressure of the medium inside the tube, and an extracorporeal circulator.

For example, in a case where a cardiac surgery is performed on a patient, an extracorporeal circulator is used. According to the extracorporeal circulator, extracorporeal blood circulation or auxiliary circulation is performed as follows. A pump is operated to remove blood from a vein of a patient via a tube. Gas exchange or temperature control in the blood is performed using an artificial lung (i.e., oxygenator). Thereafter, the blood is caused to return again to an artery or the vein of the patient via the tube. In order to properly perform the extracorporeal blood circulation or the auxiliary circulation, it is necessary to measure an intra-circuit pressure of the tube of the extracorporeal circulator by using a pressure measuring device.

For example, U.S. Pat. No. 7,748,275 B2 discloses a pressure sensor of an extracorporeal circulation circuit. The pressure sensor illustrated in FIG. 1 of the patent has a liquid chamber 6, pressure measuring means 7, and a liquid flow path 8. The liquid flow path 8 is formed as a bifurcated portion bifurcated from a portion of a tube of the extracorporeal circulation circuit, and is connected to a liquid inlet 40 of the liquid chamber 6 in a liquid-tight manner. A liquid passing through the tube is introduced into the liquid chamber 6 from the liquid flow path 8, and flows along an inner periphery of a side surface of a first connection surface 11 of the liquid chamber 6. The liquid chamber 6 has a deformation surface 20 which is at least partially deformed by a pressure inside the liquid flow path. The pressure measuring means 7 measures the pressure inside the liquid chamber 6 by measuring a deformation volume of the deformation surface 20.

The liquid chamber 6 disclosed in U.S. Pat. No. 7,748,275 has a reference surface 10 which is not deformed by the pressure inside the extracorporeal circulation circuit, and the deformation surface 20 which is located apart from the reference surface 10 and which is at least partially deformed by the pressure inside the extracorporeal circulation circuit. The liquid chamber 6 internally has a closed and liquid-tight space formed by interlocking the reference surface 10 and the deformation surface 20 with each other. In this manner, if the liquid flows into the liquid chamber 6, a load cell 45 or a strain gauge 46 disposed as the pressure measuring means 7 measures the pressure of the liquid inside the extracorporeal circulation circuit by using the deformation of the deformation surface 20.

However, according to the pressure sensor of the extracorporeal circulation circuit disclosed in U.S. Pat. No. 7,748,275, when the extracorporeal circulation or the auxiliary circulation is performed, an operator connects the liquid chamber 6 to the liquid flow path 8 by forming the liquid flow path 8 serving as the bifurcated portion in an intermediate portion of the tube of the extracorporeal circulation circuit. Then, the operator needs to carry out work for internally filling the liquid flow path 8 and the liquid chamber 6 with a liquid (blood). In this way, in order to measure an intra-circuit pressure of the liquid (blood) passing through the tube, the operator needs to carry out the work for internally filling the liquid flow path 8 and the liquid chamber 6 with the liquid in a medical treatment site or a surgical site. Therefore, when the extracorporeal circulation or the auxiliary circulation is performed, it is not easy to measure the intra-circuit pressure of the liquid (blood) passing through the tube by using the pressure sensor in the related art. In addition, the operator needs to form the liquid flow path 8 serving as the bifurcated portion in the intermediate portion of the tube as described above. Therefore, there is a possibility that an infarcted site or a thrombus of the blood may appear in the tube or the liquid flow path 8.

In contrast, a detachable pressure measuring device has been studied which is detachably mounted to the intermediate portion of the tube which is transferring the medium such as the blood. For example, the detachable pressure measuring device configured in this way includes a main body portion and a load-sensing element located in the main body portion. The main body portion is detachably mounted to the intermediate portion of the tube, and the tube is elastically deformed so as to form a flat surface. A distal sensing portion of the load-sensing element is brought into contact with the flat surface formed in the tube. In this manner, the load-sensing element measures a force by which the tube pushes back the distal sensing portion (repulsive force). Accordingly, without coming into contact with the medium, the load-sensing element can measure the intra-circuit pressure when the medium circulates.

However, the pressure measuring device having the load-sensing element which measures the repulsive force of the tube by coming into contact with the tube may malfunction in some cases. If the pressure measuring device malfunctions, there is a possibility that the intra-circuit pressure may be erroneously measured. That is, if the pressure measuring device malfunctions, the intra-circuit pressure measured by the pressure measuring device may be different from an actual intra-circuit pressure.

SUMMARY OF THE INVENTION

The present invention is made to solve the above-described problems, and an object thereof is to provide a pressure measuring device and an extracorporeal circulator, which prevent erroneous measurement of a pressure of a medium inside a tube.

According to an aspect of the present invention, in order to solve the problems, there is provided a pressure measuring device installable in a tube for transferring a medium so as to measure a pressure of the medium inside the tube. The pressure measuring device includes a main body portion mountable to the tube, polarizing means disposed in the main body portion so that light oscillating in a specific direction is transmitted therethrough, an image acquisition unit disposed in the main body portion so that image information on a pressure receiver (i.e., a pressurized body) that is deformed in response to the received pressure is acquired through the polarizing means, and a control unit that converts the image information acquired by the image acquisition unit into pressure information about the pressure.

According to the configuration, the pressure measuring device includes the image acquisition unit that acquires the image information depicting the pressurized body or receiver, which is deformed in response to received pressure, through the polarizing means disposed so that the light oscillating in the specific direction is transmitted therethrough. Then, the control unit converts the image information acquired by the image acquisition unit into the pressure information about the pressure of the medium inside the tube. That is, the pressure measuring device acquires the image information on the pressure receiver deformed in response to the received pressure, through the polarizing means, instead of using a load-sensing element which measures a repulsive force of the tube by coming into contact with the tube, and converts the image information into the pressure information. In this manner, the pressure measuring device measures the pressure of the medium inside the tube. Therefore, in a case where the pressure measuring device malfunctions, an acquisition error or a reading error of the image occurs, and the pressure of the medium inside the tube is not displayed. That is, it is possible to prevent a possibility that a false pressure different from an actual pressure of the medium may be displayed. In this manner, it is possible to prevent the pressure of the medium inside the tube from being erroneously measured.

In addition, the pressure measuring device measures the pressure of the medium inside the tube without coming into physical contact with the medium flowing inside the tube. In this manner, for example, it is possible to prevent an infarcted site or a thrombus of blood from appearing inside the tube. In addition, work for removing bubbles from the inside of the tube (bubble removal work) is simplified.

Preferably, the control unit has a storage unit which stores reference image information indicating a relationship between the image information and the pressure information, and converts the image information into the pressure information, based on the reference image information stored in the storage unit.

According to the preferred embodiment, the control unit converts the image information into the pressure information, based on the reference image information indicating the relationship between the image information and the pressure information. Therefore, the pressure measuring device can more easily perform a process of calculating the pressure of the medium inside the tube, and can accurately measure the pressure of the medium inside the tube within a shorter time.

Preferably, the pressure receiver is a thick portion of the tube. The control unit converts the image information about a distortion of the thick portion which is acquired by the image acquisition unit through the polarizing means, into the pressure information.

According to the configuration, the control unit converts the image information about the distortion of the thick portion of the tube which is acquired by the image acquisition unit through the polarizing means, into the pressure information. Therefore, even in a case where the tube is formed of a relatively hard material, the pressure measuring device can recognize a change in the distortion of the thick portion. That is, the pressure measuring device can recognize a minute change in the distortion of the thick portion through the polarizing means. In this manner, the pressure measuring device can more accurately measure the pressure of the medium inside the tube.

Preferably, the pressure measuring device according to the present invention further includes a pressure sensitive medium connected to the main body portion and the tube and serving as a pressure receiver, which is deformed in response to a received external force based on the deformation of the tube. The control unit converts the image information about the distortion of the pressure sensitive medium which is acquired by the image acquisition unit through the polarizing means, into the pressure information.

According to the preferred embodiment, the pressure measuring device further includes the pressure sensitive medium serving as the pressure receiver which is deformed in response to the external force based on the deformation of the tube. Then, the control unit converts the image information about the distortion of the pressure sensitive medium which is acquired by the image acquisition unit through the polarizing means, into the pressure information. Therefore, the pressure measuring device can recognize the minute change in the distortion of the pressure sensitive medium connected to the main body portion and the tube, through the polarizing means. In this manner, the pressure measuring device can more accurately measure the pressure of the medium inside the tube.

Preferably, the main body portion has a slip stopper which prevents a portion of the tube mounted to the main body portion from extending (e.g., slipping) in an axial direction of the tube.

According to a preferred embodiment, even in a case where the pressure of the medium inside the tube fluctuates, the slip stopper belonging to the main body portion can prevent a portion of the tube mounted to the main body portion from extending or moving in the axial direction of the tube. Therefore, the pressure measuring device can more accurately and more stably measure the pressure of inside the tube for the medium circulating in the circuit.

According to another aspect of the present invention, in order to solve the problems, there is provided an extracorporeal circulator for use in extracorporeal circulation of a medium. The extracorporeal circulator includes a tube through which the medium is transferred, and any one of the pressure measuring devices, which is disposed in the tube so as to measure the pressure of the medium inside the tube.

According to a preferred embodiment, the pressure measuring device in the extracorporeal circulator includes the image acquisition unit that acquires the image information on the pressure receiver (i.e., pressurized or deformed body), which is deformed in response to the received pressure, through the polarizing means disposed so that the light oscillating in the specific direction is transmitted therethrough. Then, the control unit converts the image information acquired by the image acquisition unit into the pressure information about the pressure of the medium inside the tube. That is, the pressure measuring device acquires the image information on the pressure receiver, which is deformed in response to the received pressure, through the polarizing means, instead of using the load-sensing element which measures the repulsive force of the tube by coming into contact with the tube, and converts the image information into the pressure information. In this manner, the pressure measuring device measures the pressure of the medium inside the tube. Therefore, in a case where the pressure measuring device malfunctions, the acquisition error or the reading error of the image occurs, and the pressure of the medium inside the tube is not displayed. That is, it is possible to prevent a possibility that the false pressure different from the actual pressure of the medium may be displayed. In this manner, it is possible to prevent the pressure of the medium inside the tube from being erroneously measured.

According to the present invention, it is possible to provide the pressure measuring device and the extracorporeal circulator which can prevent the pressure of the medium inside the tube from being erroneously measured.

DETAILED DESCRIPTION OF PREFERRED EMBODIMENTS

Figure 1:
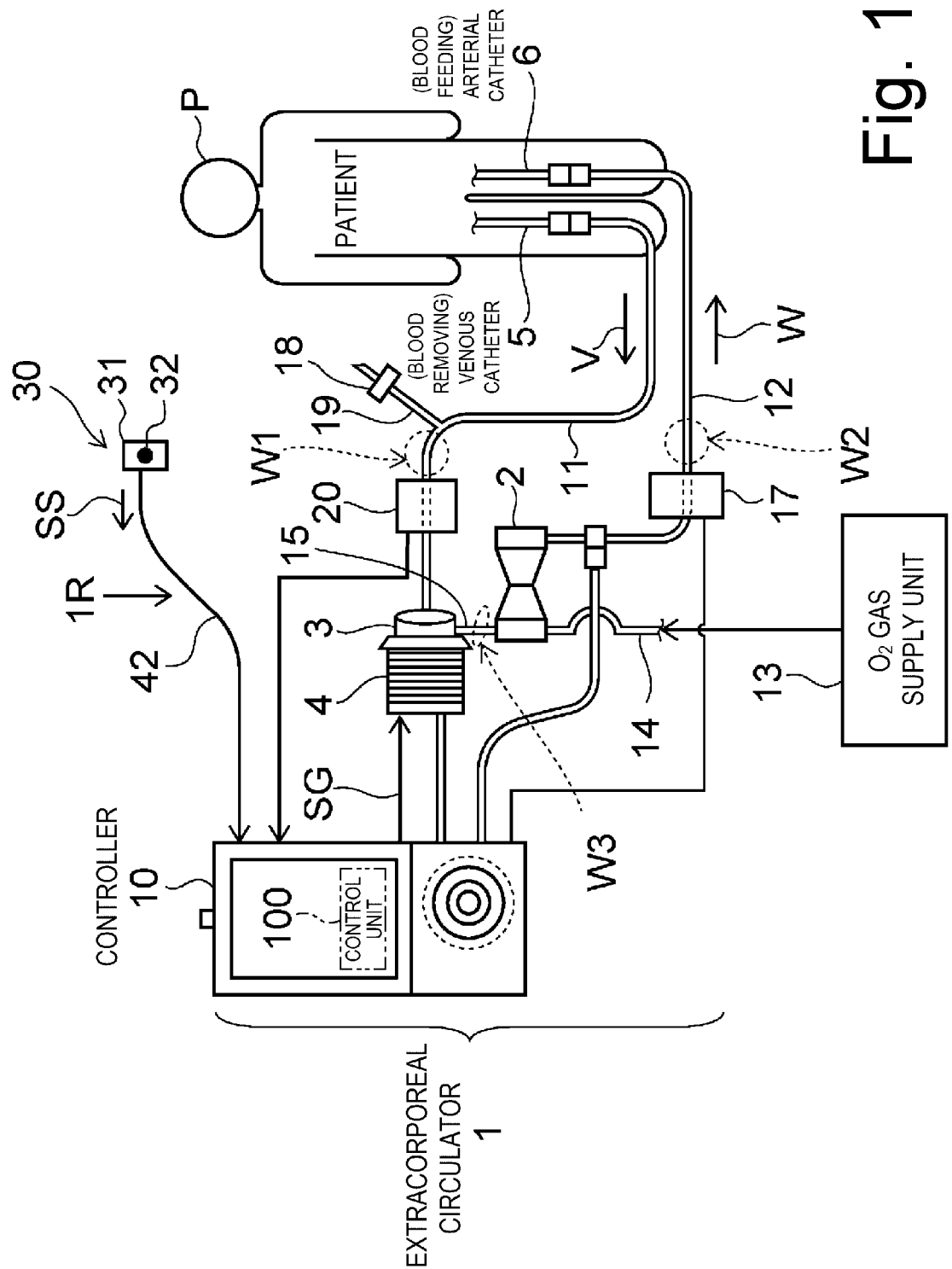
FIG. 1 is a systematic diagram illustrating an extracorporeal circulator according to an embodiment of the present invention.

Hereinafter, preferred embodiments according to the present invention will be described with reference to the drawings. The embodiments described below are preferable specific examples according to the present invention. Therefore, technically preferable limitations are imposed in various ways. However, unless otherwise particularly described in the following description, the scope of the present invention is not limited to the aspects. In addition, in each drawing, the same reference numerals will be given to the same configuration elements, and detailed description thereof will be appropriately omitted.

FIG. 1 is a systematic diagram illustrating an extracorporeal circulator according to an embodiment of the present invention. The description of "extracorporeal circulation" performed by an extracorporeal circulator 1 illustrated in FIG. 1 includes an "extracorporeal circulation operation" and an "auxiliary circulation operation". The extracorporeal circulator 1 can perform both the "extracorporeal circulation operation" and the "auxiliary circulation operation".

The "extracorporeal circulation operation" means the following. A blood circulation operation and a gas exchange operation for blood (oxygenation and/or carbon dioxide removal) are performed by the extracorporeal circulator 1, for example, in a case where cardiac blood circulation is temporarily stopped due to a cardiac surgery. In addition, the "auxiliary circulation operation" means the following. The blood circulation operation and the gas exchange operation for blood are also performed by the extracorporeal circulator 1 in a case where a heart of a patient P serving as an application target of the extracorporeal circulator 1 does not sufficiently fulfill a function or in a state where gas exchange cannot be sufficiently performed by lungs.

For example, in a case where the cardiac surgery is performed on the patient, the extracorporeal circulator 1 illustrated in FIG. 1 can perform an artificial lung extracorporeal blood circulation as follows. In the artificial lung extracorporeal blood circulation, a pump of the extracorporeal circulator 1 is operated to remove blood from a vein of the patient. The gas exchange in the blood is performed using an artificial lung, and oxygenation of the blood is performed. Thereafter, the blood subjected to oxygenation of the blood is caused to return again to an artery or the vein of the patient. The extracorporeal circulator 1 is a device which substitutes for the heart and lungs.

As illustrated in FIG. 1, the extracorporeal circulator 1 has a circulation circuit 1R for circulating the blood. The circulation circuit 1R has an artificial lung 2, a centrifugal pump 3, a drive motor (driving means) 4 that drives the centrifugal pump 3, a venous catheter (blood removing catheter) 5, an arterial catheter (blood feeding catheter) 6, and a controller 10 having a control unit 100. In addition, the extracorporeal circulator 1 includes a pressure measuring device 30. The pressure measuring device 30 corresponds to a pressure measuring device according to a first embodiment of the present invention.

As illustrated in FIG. 1, the venous catheter (blood removing catheter) 5 is inserted into a body of the patient from a femoral vein, and a distal end of the venous catheter 5 is caused to indwell a right atrium. The arterial catheter (blood feeding catheter) 6 is inserted into the body of the patient from a femoral artery. The venous catheter 5 is connected to the centrifugal pump 3 via a blood removing tube (also referred to as a blood removing line) 11. The blood removing tube 11 is a conduit for feeding the blood.

When the drive motor 4 starts to operate the centrifugal pump 3, based on a command SG of the controller 10, the centrifugal pump 3 removes the blood from the blood removing tube 11, and the blood is caused to pass through the artificial lung 2. Thereafter, the blood can return to the patient P via a blood feeding tube 12 (also referred to as a blood feeding line).

The artificial lung 2 is located between the centrifugal pump 3 and the blood feeding tube 12. The artificial lung 2 performs the gas exchange operation (oxygenation and/or carbon dioxide removal) for the blood. For example, the artificial lung 2 is a membrane type artificial lung. However, it is particularly preferably to use a hollow fiber membrane type artificial lung. Oxygen gas is supplied from an oxygen gas supply unit 13 to the artificial lung 2 through a tube 14. The blood feeding tube 12 is a conduit for connecting the artificial lung 2 and the arterial catheter 6 to each other. As the blood removing tube 11 and the blood feeding tube 12, for example, the embodiment adopts a conduit made of a synthetic resin such as a vinyl chloride resin or silicone rubber which is highly transparent, elastically deformable, and flexible. The blood serving as the liquid flows in a V-direction in the blood removing tube 11, and flows in a W-direction in the blood feeding tube 12.

In an example of the circulation circuit 1R illustrated in FIG. 1, an ultrasound bubble detection sensor 20 is located outside the blood removing tube 11 in an intermediate portion of the blood removing tube 11. In addition, a fast clamp 17 is located outside the blood feeding tube 12 in the intermediate portion of the blood feeding tube 12. In a case where the ultrasound bubble detection sensor 20 detects the presence of bubbles in the blood fed into the blood removing tube 11, the ultrasound bubble detection sensor 20 transmits a detection signal indicating that the bubbles are detected, to the controller 10. In this manner, the fast clamp 17 urgently closes the blood feeding tube 12 in order to inhibit the blood from being fed to the patient P, based on a command of the controller 10.

The ultrasound bubble detection sensor 20 can detect the bubbles mixed inside the circuit, in a case where the bubbles are mixed inside the circuit due to an erroneous operation of a three-way stopcock 18 during the blood circulation operation or breakage of a tube 19 connected to the three-way stopcock 18. If the ultrasound bubble detection sensor 20 detects the bubbles, the controller 10 illustrated in FIG. 1 notifies an operator of a warning using an alarm, or lowers the rotation speed of the centrifugal pump 3. Alternatively, the controller 10 stops the centrifugal pump 3, and transmits a command to the fast clamp 17 so that the fast clamp 17 immediately closes the blood feeding tube 12. In this manner, the controller 10 inhibits the bubbles from being fed into the body of the patient P. In this manner, the controller 10 temporarily stops the blood circulation operation in the circulation circuit 1R of the extracorporeal circulator 1, thereby preventing the bubbles from being mixed into the body of the patient P.

The pressure measuring device 30 according to the present embodiment can be mounted to any desired location of the tube 11 (12 and 15) of the circulation circuit 1R of the extracorporeal circulator 1 illustrated in FIG. 1. In this manner, when the extracorporeal circulator 1 performs the extracorporeal circulation operation or the auxiliary circulation operation on the patient P, without coming into contact with the medium, the pressure measuring device 30 can measure the intra-circuit pressure during the circulation of the medium such as the blood passing through the tube 11 (12 and 15).

The desired locations of the tube of the circulation circuit 1R on which the pressure measuring device 30 according to the present embodiment is mounted are as follows, for example. As illustrated in FIG. 1, the pressure measuring device 30 can be mounted to at least any one of a mounting position W1 in the intermediate portion of the blood removing tube 11 of the circulation circuit 1R, a mounting position W2 in the intermediate portion of the blood feeding tube 12 of the circulation circuit 1R, and a mounting position W3 in the intermediate portion of the connection tube 15 which connects the centrifugal pump 3 and the artificial lung 2 to each other.

If the pressure measuring device 30 is mounted to the mounting position W1 in the intermediate portion of the blood removing tube 11 of the circulation circuit 1R, when the extracorporeal circulation operation or the auxiliary circulation operation is performed, the intra-blood removing circuit pressure can be measured without coming into contact with the blood, during the circulation of the blood passing through the blood removing tube 11. In this manner, when the controller 10 removes the blood from the patient P via the blood removing tube 11, it is possible to understand a change trend (tendency in pressure change) in a blood removal state of the patient P in the blood removing tube 11.

In addition, if the pressure measuring device 30 is mounted to the mounting position W2 in the intermediate portion of the blood feeding tube 12 of the circulation circuit 1R, when the extracorporeal circulation operation or the auxiliary circulation operation is performed, the intra-blood feeding circuit pressure can be measured without coming into contact with the blood during the circulation of the blood passing through the blood feeding tube 12. In this manner, when the controller 10 feeds the blood to the patient P via the blood feeding tube 12, it is possible to understand a disorder of the artificial lung 2 or a change trend in a blood feeding state (tendency in pressure change) of the patient P in the blood feeding tube 12.

Furthermore, if the pressure measuring device 30 is mounted to the mounting position W3 in the intermediate portion of the connection tube 15, when the extracorporeal circulation operation and the auxiliary circulation operation is performed, the intra-blood feeding circuit pressure can be measured without coming into contact with the blood during the circulation of the blood passing through the connection tube 15 when the blood is fed by the centrifugal pump 3 via the connection tube 15. In this manner, the controller 10 can measure a change trend (tendency in pressure change) of the operation of the centrifugal pump 3 in the circulation circuit 1R.

In this way, the pressure measuring device 30 can be mounted to any desired position such as the mounting positions W1, W2, and W3 of the circulation circuit 1R. The control unit 100 of the controller 10 receives a signal SS relating to the image information acquired by the pressure measuring device 30 from the pressure measuring device 30. In this manner, the control unit 100 can measure the change trend in the intra-circuit pressure (tendency in pressure change) of the medium such as the blood in the blood removing tube 11 (blood feeding tube 12 and connection tube 15) configuring the circulation circuit 1R.

The pressure measuring device 30 according to the present embodiment has a structure which can be mounted to the tube 11 (12 and 15) in the same manner at any position, for example, such as the mounting position W1 in the intermediate portion of the blood removing tube 11 of the circulation circuit 1R illustrated in FIG. 1, the mounting position W2 in the intermediate portion of the blood feeding tube 12 of the circulation circuit 1R, and the mounting position W3 in the intermediate portion of the connection tube 15 which connects the centrifugal pump 3 and the artificial lung 2 to each other. In the following description, as an example, a case will be described where the pressure measuring device 30 according to the present embodiment is disposed at the mounting position W1 in the intermediate portion of the blood removing tube 11 of the circulation circuit 1R. In addition, for the convenience of description, the blood removing tube 11 may be simply referred to as the "tube 11".

Figure 2:
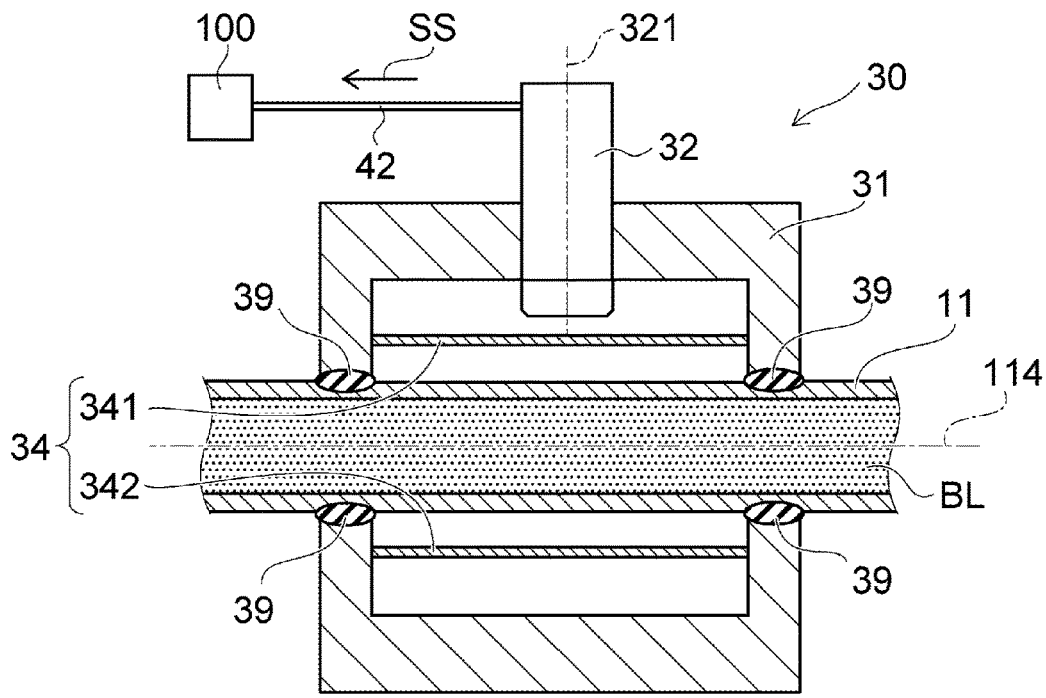
FIG. 2 is a sectional view illustrating a pressure measuring device according to a first embodiment of the present invention.
Figure 3:
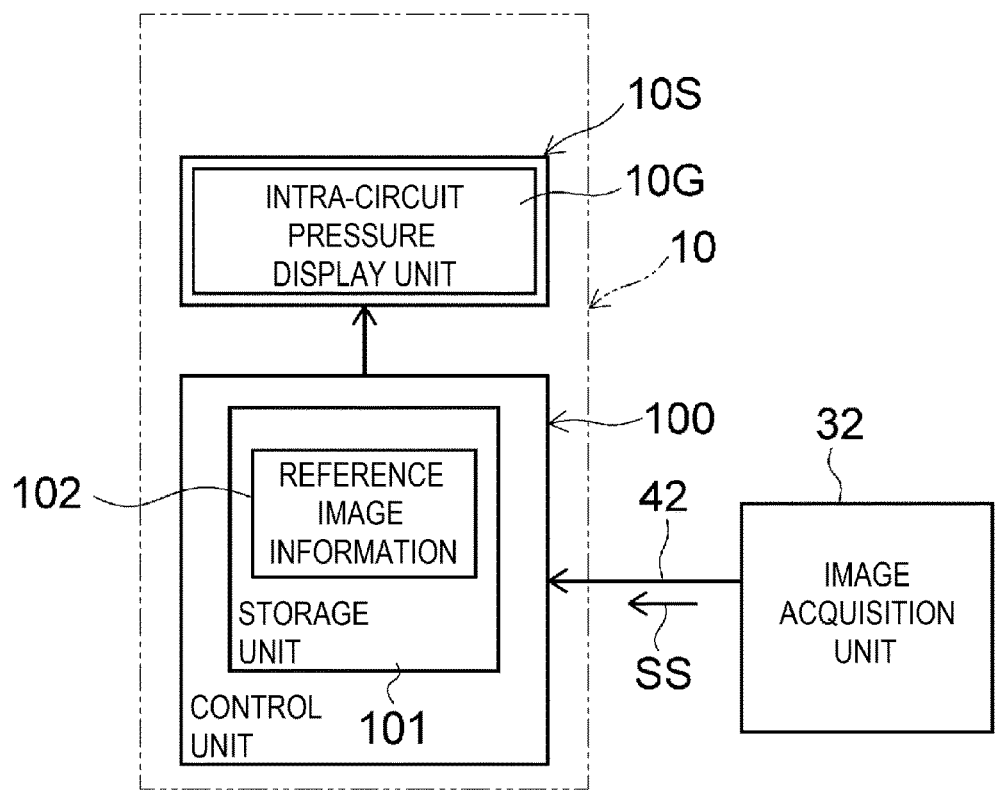
FIG. 3 is a block diagram illustrating electrical connection between a controller and the pressure measuring device.

FIG. 2 is a sectional view illustrating the pressure measuring device according to the first embodiment of the present invention. FIG. 3 is a block diagram illustrating electrical connection between the controller and the pressure measuring device.

As illustrated in FIG. 2, the pressure measuring device 30 according to the present embodiment has a main body portion 31 serving as a housing, polarizing means 34, an image acquisition unit 32, and the control unit 100 disposed in the controller 10. The control unit 100 may be disposed in the main body portion 31 instead of the controller 10.

For example, the main body portion 31 has a rectangular parallelepiped shape or a cylindrical shape, and has a structure in which the tube 11 (12 and 15) can penetrate into the main body portion 31. As a material of the main body portion 31, a rigid material may be used which can hold the blood removing tube 11, the blood feeding tube 12, and the connection tube 15 or can elastically deform the tubes in a fitted state. The material of the main body portion 31 is not particularly limited. For example, the material of the main body portion 31 includes metal or plastic. Specifically, for example, the material of the main body portion 31 includes metal such as aluminum or stainless steel. Alternatively, the material of the main body portion 31 includes plastic such as polyacetal (POM), polybutylene terephthalate (PBT), and polyethylene terephthalate (PET). In a case where the material of the main body portion 31 is transparent plastic, through the main body portion 31, an operator can visibly recognize a state where the blood removing tube 11, the blood feeding tube 12, and the connection tube 15 are held by or fitted to the main body portion 31.

The main body portion 31 has a slip stopper 39 such as an O-ring formed of rubber, for example. The slip stopper 39 is fixed into an insertion hole of the main body portion 31 through which the tube 11 passes, and a portion of the tube 11 mounted to the main body portion 31 is prevented from extending or moving in a direction of an axis 114 of the tube 11. In this manner, even in a case where a pressure of a medium BL such as the blood inside the tube 11 fluctuates, the pressure measuring device 30 can more accurately and more stably measure the pressure inside the tube 11 for the medium BL circulating in the circuit. Preferably, the two insertion holes at opposing ends of the main body portion 31 each has a respective slip stopper 39.

The polarizing means 34 has a property of transmitting the light oscillating in the specific direction therethrough, and has a first polarizing plate 341 and a second polarizing plate 342. The first polarizing plate 341 is disposed in front of the tube 11 when viewed from the image acquisition unit 32, and is fixed to the main body portion 31. That is, the first polarizing plate 341 is fixed to the main body portion 31 between the image acquisition unit 32 and the tube 11. The second polarizing plate 342 is disposed behind the tube 11 when viewed from the image acquisition unit 32, and is fixed to the main body portion 31. That is, the tube 11 is located between the first polarizing plate 341 and the second polarizing plate 342.

A polarizing component of the light transmitted through the first polarizing plate 341 intersects a polarizing component of the light transmitted through the second polarizing plate 342, and preferably both of these intersect so as to be substantially orthogonal to each other. Based on this relative arrangement, the first polarizing plate 341 and the second polarizing plate 342 are disposed inside the main body portion 31, and are fixed to the main body portion 31.

The image acquisition unit 32 is disposed in the main body portion 31. In an example illustrated in FIG. 2, the image acquisition unit 32 is fixed to the main body portion 31 in a state where an axis 321 of the image acquisition unit 32 intersects (specifically, is orthogonal to) the axis 114 of the tube 11. The image acquisition unit 32 acquires the image information depicting the pressure receiver (i.e., pressurized body), which is deformed in response to the received pressure of the medium BL inside the tube 11, through the polarizing means 34. Specifically, the image acquisition unit 32 acquires an image of the pressure receiver through the first polarizing plate 341 disposed between the image acquisition unit 32 and the tube 11. In the present specification, a scope of "acquiring the image information on the pressure receiver through the polarizing means 34" includes not only a case where the image information on the pressure receiver is acquired through both the first polarizing plate 341 and the second polarizing plate 342, but also embodiments where the image information on the pressure receiver is acquired through at least one of the first polarizing plate 341 and the second polarizing plate 342. Details of the pressure receiver will be described later. For example, the image acquisition unit 32 may include a camera using a charge-coupled device (CCD) image sensor or a complementary metal oxide semiconductor (CMOS) image sensor.

As illustrated in FIG. 3, the image acquisition unit 32 is electrically connected to the control unit 100 of the controller 10 via a signal line 42. The signal SS relating to the image information acquired (captured) by the image acquisition unit 32 is transmitted to the control unit 100 via the signal line 42. The controller 10 has a display unit 10S such as a liquid crystal display. The display unit 10S has an intra-circuit pressure display unit 10G. The intra-circuit pressure is displayed on the intra-circuit pressure display unit 10G of the controller 10.

The control unit 100 has a storage unit 101. The storage unit 101 stores (has a memory for) reference image information 102. The reference image information 102 is information for converting the image information acquired by the image acquisition unit 32 into the pressure information about the pressure of the medium BL inside the tube 11. That is, the reference image information 102 is correlation data indicating a relationship between the image information acquired by the image acquisition unit 32 and the pressure information about the pressure of the medium BL inside the tube 11. For example, the reference image information 102 may be a table for converting the image information into the pressure information. Alternatively, the reference image information 102 may be an expression based on a graph indicating the relationship between the image information and the pressure information.

The control unit 100 converts the image information acquired by the image acquisition unit 32 into the pressure information about the pressure of the medium BL inside the tube 11. That is, the control unit 100 calculates the pressure of the medium BL inside the tube 11, based on the image information acquired by the image acquisition unit 32. Specifically, based on the reference image information 102 stored in the storage unit 101, the control unit 100 converts the image information acquired by the image acquisition unit 32 into the pressure information about the pressure of the medium BL inside the tube 11. A conversion process of the control unit 100 will be further described with reference to the drawings.

Figure 4:
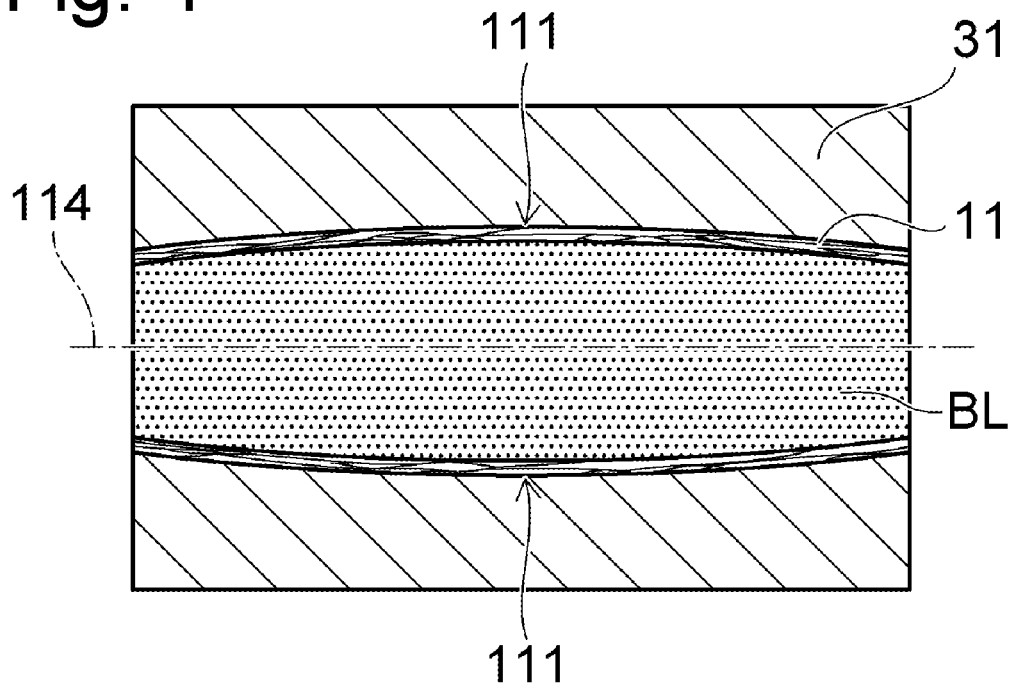
FIG. 4 is a plan view illustrating image information acquired by an image acquisition unit according to the present embodiment in a case where an intra-tube pressure is a positive-pressure.
Figure 5:
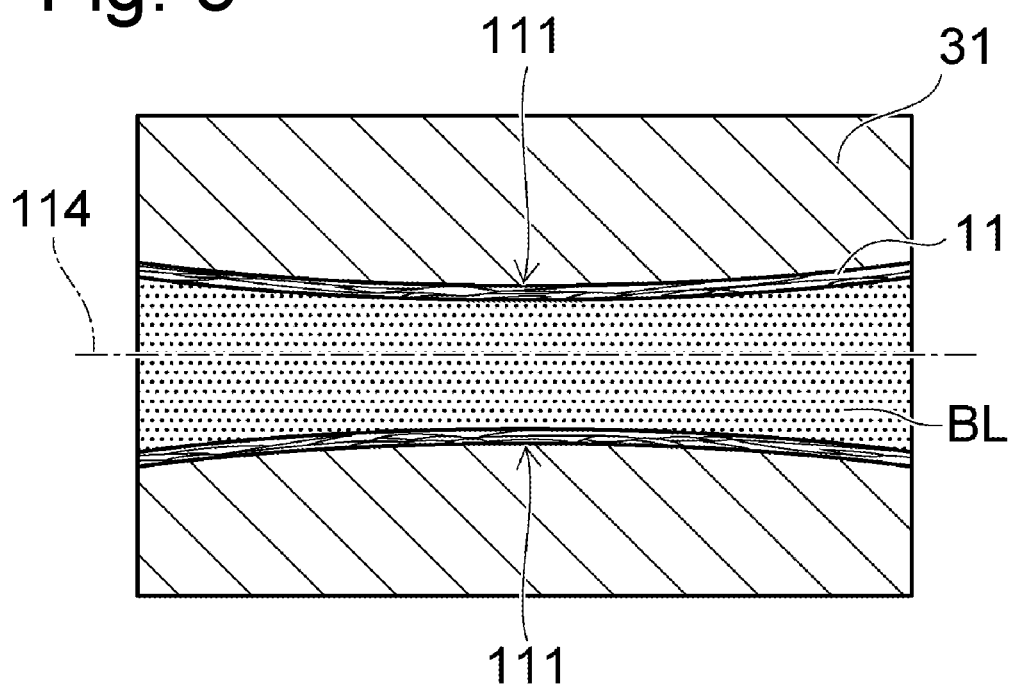
FIG. 5 is a plan view illustrating the image information acquired by the image acquisition unit according to the present embodiment in a case where the intra-tube pressure is a negative-pressure.

FIG. 4 is a plan view illustrating the image information acquired by the image acquisition unit according to the present embodiment in a case where the intra-tube pressure is a positive-pressure. FIG. 5 is a plan view illustrating the image information acquired by the image acquisition unit according to the present embodiment in a case where the intra-tube pressure is a negative-pressure.

For example, if the CCD camera images a molded product made of a synthetic resin through the polarizing plate, an internal distortion of the molded product can be confirmed in the image information captured by the camera. For example, the internal distortion of the molded product includes a residual distortion of the molded product made of the synthetic resin. The internal distortion of the molded product is changed in accordance with an external force received by the molded product (e.g., a force resulting from pressure differences on opposite sides of a wall of the molded product). In other words, if the molded product receives the external force, the internal distortion of the molded product is changed, compared to the internal distortion detected before the molded product receives the external force. Therefore, if the molded product receives the external force, the image information about the distortion detected by the camera imaging the molded product made of the synthetic resin through the polarizing plate is changed.

Here, as illustrated in FIG. 4, in a case where the pressure inside the tube 11 when the medium BL does not flow inside the tube 11 is a reference pressure (zero pressure), if the intra-circuit pressure of the medium BL passing through the tube 11 is the positive-pressure, an outer diameter of the tube 11 becomes larger than an outer diameter when the intra-circuit pressure is the reference pressure. Therefore, if the intra-circuit pressure of the medium BL passing through the tube 11 is the positive-pressure, the internal distortion of the tube 11 is changed. Then, the image information about the distortion of a thick portion 111 which is acquired by the image acquisition unit 32 through the polarizing means 34 is changed, compared to a case where the intra-circuit pressure is the reference pressure.

On the other hand, as illustrated in FIG. 5, if the intra-circuit pressure of the medium BL passing through the tube 11 is the negative-pressure, the outer diameter of the tube 11 is smaller than the outer diameter obtained when the intra-circuit pressure is the reference pressure. Therefore, if the intra-circuit pressure of the medium BL passing through the tube 11 is the negative-pressure, the internal distortion of the tube 11 is changed. Then, the image information about the distortion of the thick portion 111 which is acquired by the image acquisition unit 32 through the polarizing means 34 is changed, compared to a case where the intra-circuit pressure is the reference pressure.

The pressure measuring device 30 according to the present embodiment calculates the pressure information by recognizing such a change in the distortion of the thick portion 111 of the tube 11. That is, in an example illustrated in FIGS. 4 and 5, the thick portion 111 of the tube 11 corresponds to the "pressure receiver" according to the present invention.

Specifically, the image information about the distortion of the thick portion 111 which is acquired by the image acquisition unit 32 through the polarizing means 34 includes any desired pattern, for example, such as a stripe pattern and a patchy pattern. An example of the image information about the distortion of the thick portion 111 which is acquired by the image acquisition unit 32 through the polarizing means 34 in a case where the intra-circuit pressure of the medium BL passing through the tube 11 is the positive-pressure is as illustrated in FIG. 4. In addition, an example of the image information about the distortion of the thick portion 111 which is acquired by the image acquisition unit 32 through the polarizing means 34 in a case where the intra-circuit pressure of the medium BL passing through the tube 11 is the negative-pressure is as illustrated in FIG. 5.

On the other hand, the reference image information 102 stored in the storage unit 101 includes the image information about the distortion of the thick portion 111 which is acquired by the image acquisition unit 32 through the polarizing means 34 in a case where the intra-circuit pressure is the reference pressure (zero pressure). Therefore, the control unit 100 compares the image information about the distortion of the thick portion 111 which is acquired by the image acquisition unit 32 through the polarizing means 34 in a case where the intra-circuit pressure is at least any one of the positive-pressure and the negative-pressure, with the image information about the distortion of the thick portion 111 which is acquired by the image acquisition unit 32 through the polarizing means 34 in a case where the intra-circuit pressure is the reference pressure. Then, the control unit 100 calculates the pressure information, based on the reference image information 102 serving as the correlation data indicating the relationship between the image information about the distortion of the thick portion 111 which is acquired by the image acquisition unit 32 through the polarizing means 34 and the pressure information about the pressure of the medium BL inside the tube 11.

As described above, the pressure measuring device 30 according to the present embodiment includes the image acquisition unit 32 that acquires the image information on the pressure receiver (thick portion 111 of the tube 11 in the present embodiment) deformed in response to the received pressure, through the polarizing means 34 disposed so that the light oscillating in the specific direction is transmitted therethrough. Then, the control unit 100 converts the image information acquired by the image acquisition unit 32 into the pressure information about the pressure of the medium inside the tube 11. That is, the pressure measuring device 30 acquires the image information on the pressure receiver, which is deformed in response to the received pressure, through the polarizing means 34, instead of using the load-sensing element which measures the repulsive force of the tube 11 by coming into contact with the tube 11, and converts the image information into the pressure information. In this manner, the pressure measuring device 30 measures the pressure of the medium inside the tube 11. Therefore, in a case where the pressure measuring device 30 malfunctions, the acquisition error or the reading error of the image occurs, and the pressure of the medium inside the tube 11 is not displayed. That is, it is possible to prevent a possibility that the false pressure different from the actual pressure of the medium may be displayed. In this manner, it is possible to prevent the pressure of the medium inside the tube 11 from being erroneously measured.

In addition, the pressure measuring device 30 measures the pressure of the medium BL inside the tube 11 without coming into contact with the medium BL flowing inside the tube 11. In this manner, for example, it is possible to prevent an infarcted site or a thrombus of the blood from appearing inside the tube 11. In addition, work for removing bubbles from the inside of the tube 11 (bubble removal work) is simplified.

In addition, the control unit 100 converts the image information into the pressure information, based on the reference image information 102 indicating the relationship between the image information and the pressure information. Therefore, the pressure measuring device 30 can more easily perform a process of calculating the pressure of the medium BL inside the tube 11, and can accurately measure the pressure of the medium BL inside the tube 11 within a shorter time.

Furthermore, the control unit 100 converts the image information about the distortion of the thick portion 111 which is acquired by the image acquisition unit 32 through the polarizing means 34, into the pressure information. Therefore, even in a case where the tube 11 is formed of a relatively hard material, the pressure measuring device 30 can recognize a change in the distortion of the thick portion 111. That is, for example, in a case where the tube 11 is formed of a flexible synthetic resin such as a vinyl chloride resin or silicone rubber, the tube 11 can be flexibly deformed in accordance with the pressure of the medium BL inside the tube 11. That is, a deformation volume of the tube 11 is relatively large. Therefore, the pressure measuring device 30 is likely to measure pressure fluctuations in the medium inside the tube 11. On the other hand, the deformation volume of the tube 11 is relatively large. Accordingly, the tube 11 may be degraded relatively fast. In contrast, in a case where the tube 11 is formed of a relatively hard material, whereas the tube 11 is degraded relatively slowly, the deformation volume of the tube 11 is relatively small.

Therefore, the pressure measuring device 30 may be less likely to measure the pressure fluctuations in the medium inside the tube 11. Therefore, according to the pressure measuring device 30 of the present embodiment, the image acquisition unit 32 acquires the image information about the distortion of the thick portion 111, through the polarizing means 34. Then, the control unit 100 converts the image information about the distortion of the thick portion 111 which is acquired by the image acquisition unit 32 through the polarizing means 34, into the pressure information. Therefore, even in a case where the tube 11 is formed of a relatively hard material, the pressure measuring device 30 can recognize a change in the distortion of the thick portion 111. That is, the pressure measuring device 30 can recognize a minute change in the distortion of the thick portion 111 through the polarizing means 34. In this manner, the pressure measuring device 30 can more accurately measure the pressure of the medium inside the tube 11.

Next, a second embodiment according to the present invention will be described. In a case where configuration elements of a pressure measuring device 30A according to the second embodiment are the same as configuration elements of the pressure measuring device 30 according to the first embodiment described above with reference to FIGS. 1 to 5, repeated description will be appropriately omitted, and different points will be mainly described below.

Figure 6:
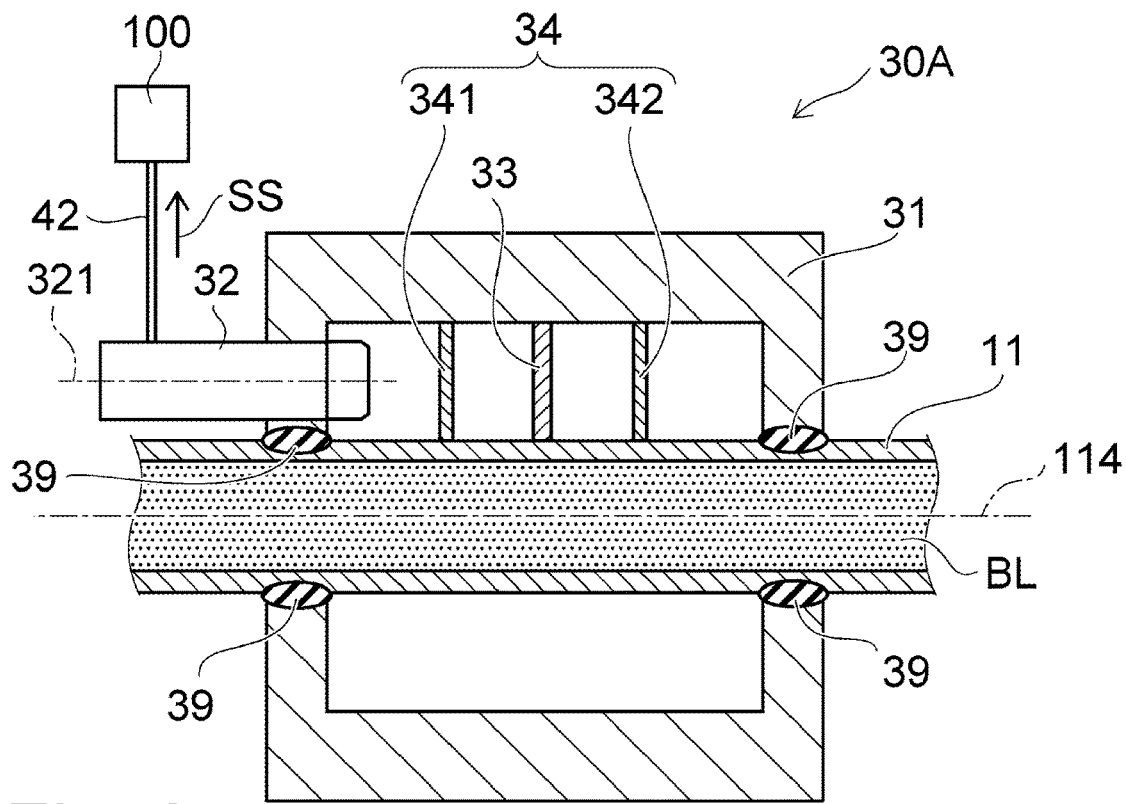
FIG. 6 is a sectional view illustrating a pressure measuring device according to a second embodiment of the present invention.
Figure 7:
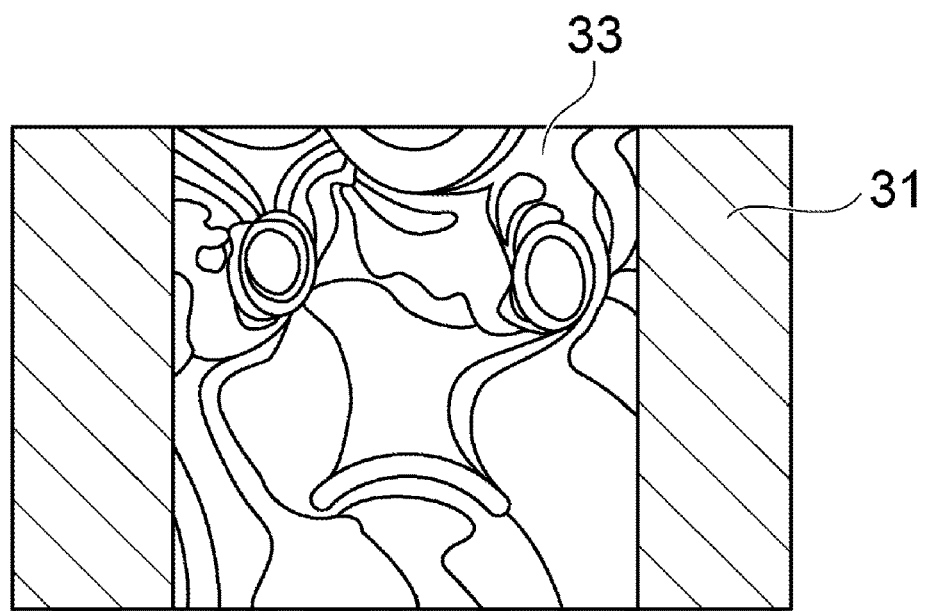
FIG. 7 is a plan view illustrating the image information acquired by the image acquisition unit according to the present embodiment in a case where the intra-tube pressure is the positive-pressure.
Figure 8:
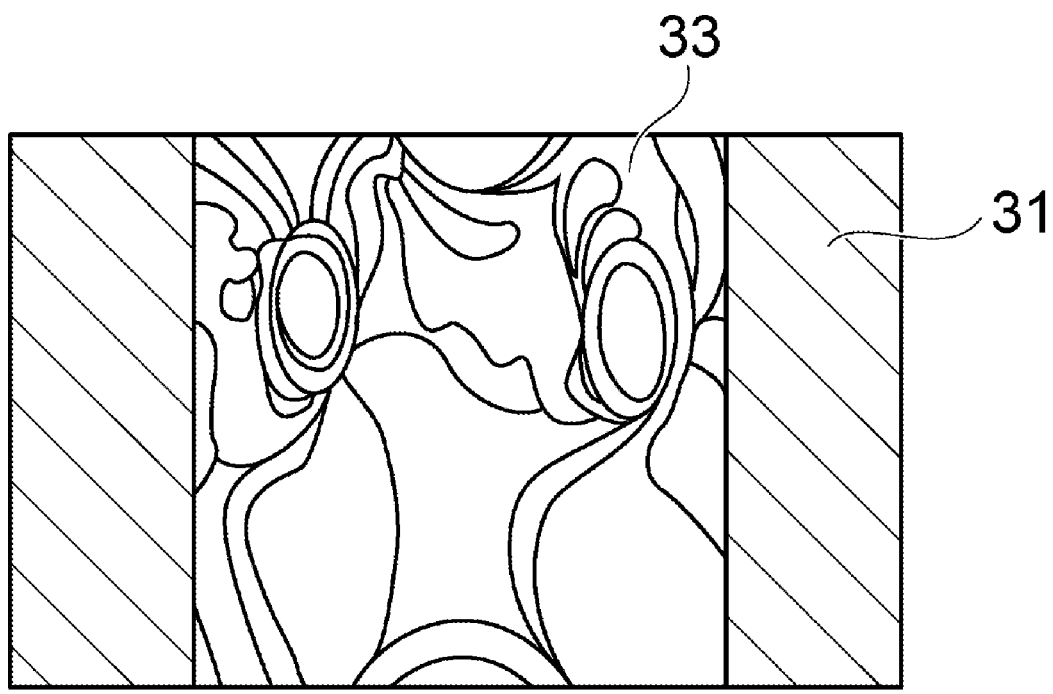
FIG. 8 is a plan view illustrating the image information acquired by the image acquisition unit according to the present embodiment in a case where the intra-tube pressure is the negative-pressure.

FIG. 6 is a sectional view illustrating the pressure measuring device according to the second embodiment of the present invention. FIG. 7 is a plan view illustrating the image information acquired by the image acquisition unit according to the present embodiment in a case where the intra-tube pressure is the positive-pressure. FIG. 8 is a plan view illustrating the image information acquired by the image acquisition unit according to the present embodiment in a case where the intra-tube pressure is the negative-pressure.

As illustrated in FIG. 6, the pressure measuring device 30A according to the present embodiment has the main body portion 31 serving as a housing, the polarizing means 34, the image acquisition unit 32, a pressure sensitive medium (pressurized body or pressure receiver) 33, and the control unit 100 disposed in the controller 10. The pressure sensitive medium 33 according to the present embodiment corresponds to the "pressure receiver" according to the present invention. The image acquisition unit 32 is fixed to the main body portion 31 in a state where the axis 321 of the image acquisition unit 32 is parallel to the axis 114 of the tube 11.

The polarizing means 34 has a property of transmitting the light oscillating in the specific direction therethrough, and has the first polarizing plate 341 and the second polarizing plate 342. The first polarizing plate 341 is disposed in front of the pressure sensitive medium 33 when viewed from the image acquisition unit 32, and is fixed to the main body portion 31. That is, the first polarizing plate 341 is fixed to the main body portion 31 between the image acquisition unit 32 and the pressure sensitive medium 33. The second polarizing plate 342 is disposed behind the pressure sensitive medium 33 when viewed from the image acquisition unit 32, and is fixed to the main body portion 31. That is, the pressure sensitive medium 33 is fixed to the main body portion 31 between the first polarizing plate 341 and the second polarizing plate 342.

The pressure measuring device 30A according to the present embodiment is different from the pressure measuring device 30 according to the first embodiment in that the pressure measuring device 30A includes the pressure sensitive medium 33, and in that the axis 321 of the image acquisition unit 32 is parallel to the axis 114 of the tube 11. In addition, the pressure measuring device 30A according to the present embodiment is different from the pressure measuring device 30 according to the first embodiment in that the polarizing means 34 has a different installation form. Other structures are the same as structures of the pressure measuring device 30 according to the first embodiment.

The pressure sensitive medium 33 is connected to the main body portion 31 and the tube 11. For example, the pressure sensitive medium 33 is fixed to the main body portion 31 by being bonded, fused, or fitted to the main body portion 31. In addition, the pressure sensitive medium 33 is fixed to the tube 11 by being bonded or fused to the tube 11. The pressure sensitive medium 33 is deformed in response to the received external force based on the deformation of the tube 11. A material of the pressure sensitive medium 33 is not particularly limited as long as the pressure sensitive medium 33 is deformed in response to the received external force based on the deformation of the tube 11. For example, the material of the pressure sensitive medium 33 includes plastic such as polyacetal (POM), polybutylene terephthalate (PBT), and polyethylene terephthalate (PET). Alternatively, the material of the pressure sensitive medium 33 may be an elastically deformable and flexible synthetic resin (for example, a vinyl chloride resin or silicone rubber), similarly to the tube 11.

As described above with reference to FIGS. 4 and 5, if the intra-circuit pressure of the medium BL passing through the tube 11 is the positive-pressure, the outer diameter of the tube 11 is larger than the outer diameter obtained when the intra-circuit pressure is the reference pressure. Then, a space between the main body portion 31 and the tube 11 is narrower than a space obtained when the intra-circuit pressure is the reference pressure. Therefore, the pressure sensitive medium 33 is subjected to compressive deformation in response to the received external force based on expansion deformation of the tube 11. The image acquisition unit 32 acquires the image information about the distortion of the pressure sensitive medium 33 through the polarizing means 34, and transmits the signal SS relating to the image information to the control unit 100 via the signal line 42. An example of the image information about the distortion of the pressure sensitive medium 33 which is acquired by the image acquisition unit 32 through the polarizing means 34 in a case where the intra-circuit pressure of the medium BL passing through the tube 11 is the positive-pressure is as illustrated in FIG. 7.

On the other hand, if the intra-circuit pressure of the medium BL passing through the tube 11 is the negative-pressure, the outer diameter of the tube 11 is smaller than the outer diameter obtained when the intra-circuit pressure is the reference pressure. Then, the space between the main body portion 31 and the tube 11 is wider than the space obtained when the intra-circuit pressure is the reference pressure. Therefore, the pressure sensitive medium 33 is subjected to stretching deformation in response to the received external force based on shrinkage deformation of the tube 11. The image acquisition unit 32 acquires the image information about the distortion of the pressure sensitive medium 33 through the polarizing means 34, and transmits the signal SS relating to the image information to the control unit 100 via the signal line 42. An example of the image information about the distortion of the pressure sensitive medium 33 which is acquired by the image acquisition unit 32 through the polarizing means 34 in a case where the intra-circuit pressure of the medium BL passing through the tube 11 is the negative-pressure is as illustrated in FIG. 8.

On the other hand, the reference image information 102 stored in the storage unit 101 includes the image information about the distortion of the pressure sensitive medium 33 which is acquired by the image acquisition unit 32 through the polarizing means 34 in a case where the intra-circuit pressure is the reference pressure (zero pressure). Therefore, the control unit 100 compares the image information about the distortion of the pressure sensitive medium 33 which is acquired by the image acquisition unit 32 through the polarizing means 34 in a case where the intra-circuit pressure is at least any one of the positive-pressure and the negative-pressure, with the image information about the distortion of the pressure sensitive medium 33 which is acquired by the image acquisition unit 32 through the polarizing means 34 in a case where the intra-circuit pressure is the reference pressure. Then, the control unit 100 calculates the pressure information, based on the reference image information 102 serving as the correlation data indicating the relationship between the image information about the distortion of the pressure sensitive medium 33 which is acquired by the image acquisition unit 32 through the polarizing means 34 and the pressure information about the pressure of the medium BL inside the tube 11.

According to the pressure measuring device 30A of the present embodiment, the control unit 100 converts the image information about the distortion of the pressure sensitive medium 33 which is acquired by the image acquisition unit 32 through the polarizing means 34, into the pressure information. Therefore, the pressure measuring device 30A can recognize a minute change in the distortion of the pressure sensitive medium 33 connected to the main body portion 31 and the tube 11, through the polarizing means 34. In this manner, the pressure measuring device 30A can more accurately measure the pressure of the medium inside the tube 11.

As described above, in the pressure measuring device 30 according to the first embodiment and the pressure measuring device 30A according to the second embodiment, the control unit 100 converts the image information acquired by the image acquisition unit 32 into the pressure information about the pressure of the medium BL inside the tube 11. Therefore, in a case where the pressure measuring devices 30 and 30A malfunction, the acquisition error or the reading error of the image occurs, and the pressure of the medium BL inside the tube 11 is not displayed on the intra-circuit pressure display unit 10G. That is, it is possible to prevent a possibility that the false pressure different from the actual pressure of the medium BL may be displayed on the intra-circuit pressure display unit 10G. In this manner, it is possible to prevent the pressure of the medium BL inside the tube 11 from being erroneously measured.

In addition, the extracorporeal circulator 1 according to the present embodiment includes the tube 11 (12 and 15) for transferring the medium BL, and the pressure measuring device 30 (30A) disposed in the tube 11 (12, 15) so as to measure the pressure of the medium BL inside the tube 11 (12 and 15). In this manner, the same advantageous effects as the above-described advantageous effects of the pressure measuring device 30 (30A) according to the present embodiment can be obtained.

Hitherto, the embodiments according to the present invention have been described. However, the present invention is not limited to the above-described embodiments, and can be modified in various ways within the scope not departing from the scope of the appended claims. The configurations of the above-described embodiments can be partially omitted, or can be optionally combined with each other so as to be different from the above-described configurations. In the present embodiment, as an example, a case has been described where the pressure measuring devices 30 and 30A are disposed at the mounting position W1 in the intermediate portion of the blood removing tube 11 in the circulation circuit 1R. The above-described advantageous effects according to the present embodiment can be similarly obtained, even in a case where the pressure measuring devices 30 and 30A are disposed at any position of the mounting position W2 in the intermediate portion of the blood feeding tube 12 in the circulation circuit 1R and the mounting position W3 in the intermediate portion of the connection tube 15 for connecting the centrifugal pump 3 and the artificial lung 2 to each other.

What is claimed is:

1. A pressure measuring device configured for installation in a circulation circuit having a conduit for transferring a pumped liquid medium so as to measure a pressure of the pumped liquid medium inside the circulation circuit, comprising:
a main body portion adapted to detachably and movably mount onto an outer periphery of the conduit;
an elastically-deformable pressure receiver body within the main body portion adapted to deform according to the pressure of the pumped liquid medium;
a polarizer disposed in the main body portion so that light oscillating in a predetermined direction passes therethrough;
an image acquisition unit disposed in the main body portion to acquire image information of the elastically-deformable pressure receiver body through the polarizer as the elastically-deformable pressure receiver body is deformed in response to the pressure of the pumped liquid medium; and
a control unit configured to convert the image information acquired by the image acquisition unit into pressure information.

2. The pressure measuring device according to claim 1:
wherein the control unit has a storage unit configured to store reference image information indicating a relationship between the image information and the pressure information, and wherein the control unit is configured to convert the image information into the pressure information based on the reference image information stored in the storage unit.

3. The pressure measuring device according to claim 1:
wherein the conduit is comprised of an elastically-deformable tube conveying the pumped liquid medium;
wherein the elastically-deformable tube is captured inside the main body portion;
wherein the elastically-deformable pressure receiver body is comprised of a portion of the elastically-deformable tube; and
wherein the control unit configured to convert, into the pressure information, the image information about a distortion of the tube portion which is acquired by the image acquisition unit through the polarizer.

4. The pressure measuring device according to claim 1 wherein the conduit is comprised of an elastically-deformable tube conveying the pumped liquid medium and captured inside the main body portion, the pressure measuring device further comprising:
a pressure sensitive medium connected between the main body portion and the elastically-deformable tube and configured to serve as the elastically-deformable pressure receiver body configured to be deformed in response to a received external force based on a deformation of the elastically-deformable tube;
wherein the control unit is configured to convert the image information about a distortion of the pressure sensitive medium which is acquired by the image acquisition unit through the polarizer into the pressure information.

5. The pressure measuring device according to claim 1:
wherein the main body portion has a slip stopper configured to prevent a portion of the conduit mounted to the main body portion from extending in an axial direction of the conduit.

6. An extracorporeal circulator for use in extracorporeal circulation of blood, comprising:
a circulation circuit having a conduit through which the blood is transferred; and
a pressure measuring device comprising:
an main body portion adapted to detachably and movably mount onto the conduit;
an elastically-deformable pressure receiver body within the main body portion adapted to deform according to the pressure of the blood;
a polarizer disposed in the main body portion so that light oscillating in a predetermined direction passes therethrough;
an image acquisition unit disposed in the main body portion to acquire image information of the elastically-deformable pressure receiver body through the polarizer as the elastically-deformable pressure receiver body is deformed in response to the pressure of the blood; and
a control unit configured to convert the image information acquired by the image acquisition unit into pressure information.

7. The extracorporeal circulator according to claim 6:
wherein the control unit has a storage unit configured to store reference image information indicating a relationship between the image information and the pressure information, and wherein the control unit is configured to convert the image information into the pressure information based on the reference image information stored in the storage unit.

8. The extracorporeal circulator according to claim 6:
wherein the conduit is comprised of an elastically-deformable tube conveying the blood;
wherein the elastically-deformable tube is captured inside the main body portion;
wherein the elastically-deformable pressure receiver body is comprised of a portion of the elastically-deformable tube; and
wherein the control unit configured to convert, into the pressure information, the image information about a distortion of the portion of the elastically-deformable tube which is acquired by the image acquisition unit through the polarizer.

9. The extracorporeal circulator according to claim 6 wherein the conduit is comprised of an elastically-deformable tube conveying the blood and captured inside the main body portion, the pressure measuring device further comprising:
a pressure sensitive medium connected between the main body portion and the elastically-deformable tube and configured to serve as the elastically-deformable pressure receiver body configured to be deformed in response to a received external force based on a deformation of the elastically-deformable tube;
wherein the control unit is configured to convert the image information about a distortion of the pressure sensitive medium which is acquired by the image acquisition unit through the polarizer into the pressure information.

10. The extracorporeal circulator according to claim 6:
wherein the main body portion has a slip stopper configured to prevent a portion of the conduit mounted to the main body portion from extending in an axial direction of the conduit.

11. A method of detecting blood pressure in an elastically-deformable tube conveying pumped blood in an extracorporeal circulator, comprising the steps of:
capturing a portion of the elastically-deformable tube in a pressure measuring device having a main body portion adapted to detachably and movably mount onto the tube, a polarizer disposed in the main body portion so that light oscillating in a predetermined direction passes therethrough, and an image acquisition unit disposed in the main body portion to acquire image information of a pressure receiver body through the polarizer, wherein the pressure receiver body is arranged to deform according to a pressure of the pumped blood;
pumping the blood through the elastically-deformable tube;
capturing image information of the pressure receiver body through the polarizer as the pressure receiver body is deformed; and
comparing the image information acquired by the image acquisition unit with stored reference image information to determine the blood pressure, wherein the reference image information defines a relationship between deformation represented by the reference image information and corresponding pressure information.

12. The method of claim 11 wherein the pressure receiver body is comprised of a capture portion of the elastically-deformable tube.

13. The method of claim 11 wherein the pressure receiver body is comprised of a pressure sensitive medium connected between the main body portion and the elastically-deformable tube and configured to serve as the pressure receiver body configured to be deformed in response to a received external force based on a deformation of the elastically-deformable tube.

* * * * *